US007867203B2

(12) United States Patent
Rosenberg et al.

(10) Patent No.: US 7,867,203 B2
(45) Date of Patent: Jan. 11, 2011

(54) IMPLANTABLE PUMP WITH ADJUSTABLE FLOW RATE

(75) Inventors: Meir Rosenberg, Newton, MA (US); Douglas MacBride, Walpole, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 0 days.

(21) Appl. No.: 12/042,037

(22) Filed: Mar. 4, 2008

(65) Prior Publication Data
US 2008/0154215 A1    Jun. 26, 2008

Related U.S. Application Data

(62) Division of application No. 10/656,600, filed on Sep. 5, 2003, now Pat. No. 7,367,968.

(51) Int. Cl.
*A61M 5/00* (2006.01)

(52) U.S. Cl. ...................................... 604/246
(58) Field of Classification Search ................ 604/247, 604/250, 890.1–892.1; 417/44.9, 132; 137/625.12, 137/863; 251/5
See application file for complete search history.

(56) References Cited

U.S. PATENT DOCUMENTS

| | | | | |
|---|---|---|---|---|
| 3,690,344 A | * | 9/1972 | Brumm .................. | 137/625.28 |
| 3,726,313 A | * | 4/1973 | Pandya ........................ | 137/872 |
| 3,771,563 A | * | 11/1973 | Hayner .................. | 137/625.28 |
| 3,794,068 A | * | 2/1974 | Milroy ........................ | 137/497 |
| 3,951,168 A | * | 4/1976 | Roberts .................. | 137/625.28 |
| 4,147,183 A | * | 4/1979 | Kalsi .................. | 137/625.28 |
| 4,299,220 A | * | 11/1981 | Dorman ...................... | 604/118 |
| 4,443,218 A | | 4/1984 | DeCant et al. | |
| 4,447,224 A | | 5/1984 | DeCant, Jr. et al. | |
| 4,718,893 A | | 1/1988 | Dorman et al. | |
| 4,931,050 A | | 6/1990 | Idriss | |
| 5,116,308 A | * | 5/1992 | Hagiwara .................. | 604/6.15 |

(Continued)

FOREIGN PATENT DOCUMENTS

DE    1045194    11/1958

(Continued)

OTHER PUBLICATIONS

European Search Report (EP 04 25 5345) dated Jan. 19, 2005.

*Primary Examiner*—Nicholas D Lucchesi
*Assistant Examiner*—Nathan R Price
(74) *Attorney, Agent, or Firm*—Nutter McClennen & Fish LLP

(57) ABSTRACT

A valve that is adapted to control the flow rate of fluid flow from an implantable pump or other fluid delivery device is provided. In general, the valve includes a multi-lumen member that is adapted to receive fluid-flow therethrough, and a restrictor member that is coupled to the multi-lumen member such that the restrictor member is effective to selectively restrict at least a portion of one or more lumens in the multi-lumen member to thereby adjust the flow rate of fluid flowing through the multi-lumen member. The valve can be built into an implantable drug pump to control fluid flow exiting the pump, or alternatively the valve can disposed within a catheter or otherwise coupled to an outlet port in an implantable drug pump to control the flow rate of fluid exiting the drug pump.

21 Claims, 3 Drawing Sheets

U.S. PATENT DOCUMENTS

| | | |
|---|---|---|
| 5,667,504 A | 9/1997 | Baumann et al. |
| 5,820,589 A | 10/1998 | Torgerson et al. |
| 5,908,414 A | 6/1999 | Otto et al. |
| 5,937,895 A | 8/1999 | Le Febre et al. |
| 6,007,609 A | 12/1999 | Semerdjian et al. |
| 6,045,115 A | 4/2000 | Martin, Jr. et al. |
| 6,048,328 A | 4/2000 | Haller et al. |
| 6,174,352 B1 | 1/2001 | Semerdjian et al. |
| 6,333,088 B1 | 12/2001 | Le Febre et al. |
| 6,471,675 B1 | 10/2002 | Rogers et al. |
| 7,367,968 B2 | 5/2008 | Rosenberg et al. |

FOREIGN PATENT DOCUMENTS

| | | |
|---|---|---|
| WO | 0156633 | 8/2002 |

* cited by examiner

IMPLANTABLE PUMP WITH ADJUSTABLE FLOW RATE

CROSS REFERENCE TO RELATED APPLICATIONS

This application is a divisional of U.S. patent application Ser. No. 10/656,600 filed on Sep. 5, 2003 and entitled "Implantable Pump with Adjustable Flow Rate," which is hereby incorporated by reference in its entirety.

FIELD OF THE INVENTION

The present invention relates to an implantable pump having a continuous fluid flow with an adjustable flow rate.

BACKGROUND OF THE INVENTION

Implantable drug delivery devices are commonly used to provide site specific and/or sustained delivery of beneficial agents to address adverse patient conditions. The pumps are used for the continuous medication delivery over relatively long periods of time in patients who could otherwise only be treated by injecting the medications, such as, e.g., morphines, heparins and similar drugs, several times daily. Pumps are advantageous in comparison with injections in that an even flow rate and a significantly lower total intake of the drug can be realized.

Implantable drug pumps typically include a reservoir for storing a fluid, such as a drug, and a pump or other flow control device to deliver the fluid to a site within a patient. A septum is formed on the top of the pump to allow refilling of the reservoir. Most implantable pumps also include a bolus port which is coupled to the catheter to enable a one-time injection directly to the treatment site. In use, the pump is disposed in a subcutaneous pocket in the area of the abdomen of the patient whereby the refill opening sealed by the septum is palpable under the skin of the patient. The medication reservoir is filled by piercing the skin of the patient and the septum with the corresponding needle of a syringe.

During treatment for certain medical conditions, the amount of medication being delivered from the pump may need to be adjusted. Accordingly, variable flow rate programmable pumps have been developed that allow the flow rate to be adjusted over time. These pumps typically include a battery as an energy source that is used to open and close a valve to adjust the flow rate. While these pumps provide some advantages over fixed flow rate pumps, the use of such pumps has some drawbacks. In particular, variable flow rate pumps have a normal life that is limited by the life of the battery. Since these pumps require an active pumping mechanism or an active valve to control flow rate, the pumps tend to be inefficient as they consume energy to operate the pump. After that, removal of the pump is necessary in order to renew the energy source. Further, in order to guard against the shortening of the device's useful life, variable flow rate pumps are typically not manufactured with additional power-consuming features such as sensors and other diagnostic equipment which would provide useful for monitoring the patient during treatment. One other problem associated with current variable flow rate pumps is that they only allow for a limited number of pre-set flow rates.

Accordingly, there remains a need for an implantable pump having an adjustable flow rate, and that has an extended useful life.

SUMMARY OF THE INVENTION

The present invention provides a valve that is adapted to control the flow rate of fluid flow from an implantable pump. The valve generally includes a multi-lumen member, such as a multi-lumen capillary tube, that is adapted to receive fluid-flow therethrough, and a restrictor member that is coupled to the multi-lumen member such that the restrictor member is effective to selectively restrict at least a portion of one or more lumens in the multi-lumen member to thereby adjust the flow rate of fluid flowing through the multi-lumen member.

In one embodiment, the multi-lumen member can include a first end coupled to an inlet port for receiving fluid flow from an implantable pump, and a second, opposed end having an outlet port for delivering fluid to a fluid-delivery catheter. The restrictor member is preferably a flexible membrane that is disposed adjacent to one of the first end or the second end of the capillary tube, and that is effective to selectively restrict at least a portion of one or more lumens in the capillary tube. The valve can also include an actuator mechanism for applying a force to the flexible membrane to selectively restrict at least a portion of one or more lumens in the capillary tube. The actuator mechanism is preferably a mechanical or electromechanical member.

In another embodiment, the flexible membrane is expandable or positionable to selectively restrict at least a portion of one or more lumens in the capillary tube. The flexible membrane can also or alternatively be coupled to a housing to form a balloon-like structure such that the flexible membrane is inflatable to selectively restrict at least a portion of one or more lumens in the capillary tube. A hydraulic pump can be coupled to the flexible membrane to selectively inflate and/or deflate the flexible membrane, and an actuator mechanism can be coupled to the hydraulic pump for selectively actuating the hydraulic pump. The actuator mechanism is preferably operable by telemetry.

The present invention also provides an implantable drug-delivery pump that includes a housing having a reservoir adapted to retain a fluid therein, a pump inlet port formed in the housing for delivering fluid to the reservoir, a reservoir outlet port formed in the housing and adapted to receive fluid from the reservoir, a driver mechanism effective to drive fluid from the reservoir to the reservoir outlet port, and a valve in fluid communication with the reservoir outlet port. The valve includes a multi-lumen member coupled to a restrictor member that is adapted to selectively restrict at least a portion of one or more lumens in the multi-lumen member to thereby adjust the flow rate of fluid flowing from the reservoir.

In one embodiment, the valve can be disposed within the housing. In this configuration, the multi-lumen member can be, for example, a multi-lumen capillary tube that preferably includes a first end coupled to the reservoir outlet port for receiving fluid flow from the reservoir, and a second, opposed end coupled to a pump outlet port for delivering fluid to a fluid-delivery catheter. In an alternative embodiment, the valve can be disposed within a fluid delivery catheter that is coupled to a pump outlet port formed in the housing and in fluid communication with the reservoir outlet port. The multi-lumen member can be a multi-lumen capillary tube that is disposed within a catheter and that includes a first end coupled to the pump outlet port, and a second, opposed end coupled to the fluid delivery catheter for delivering fluid to a patient.

In yet another embodiment, the multi-lumen member can be a multi-lumen capillary tube, and the restrictor member can be a flexible membrane that is disposed adjacent to one of a first end or a second end of the capillary tube. The flexible membrane is effective to selectively restrict at least a portion of one or more lumens in the capillary tube. An actuator mechanism can optionally be provided for applying pressure to the flexible membrane to selectively restrict at least a portion of one or more lumens in the capillary tube. The actuator mechanism can be, for example, a mechanical or electromechanical member.

In yet another embodiment, the flexible membrane is expandable to selectively restrict at least a portion of one or more lumens in the capillary tube. More particularly, the flexible membrane can be coupled to a housing to form a balloon-like structure such that the flexible membrane is inflatable to selectively restrict at least a portion of one or more lumens in the capillary tube. A hydraulic pump can be coupled to the flexible membrane to selectively inflate and/or deflate the flexible membrane.

In other aspects of the present invention, the implantable drug-delivery pump can include an orifice disposed downstream of the valve and in fluid communication with the valve. The orifice includes a differential pressure sensor that is effective to measure the flow rate of fluid through the orifice.

Methods for controlling the flow rate of fluid being delivered to a patient from an implantable pump are also provided.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention generally provides a valve that is adapted to control the flow rate of fluid flow from an implantable pump or another fluid delivery device. In general, the valve includes a multi-lumen member that is adapted to receive fluid-flow therethrough, and a restrictor member that is coupled to the multi-lumen member such that the restrictor member is effective to selectively restrict at least a portion of one or more lumens in the multi-lumen member to thereby adjust the flow rate of fluid flowing through the multi-lumen member. The valve can be built into an implantable drug pump to control fluid flow exiting the pump, or alternatively the valve can disposed within a catheter or otherwise coupled to an outlet port in an implantable drug pump to control the flow rate of fluid exiting the drug pump.

The device is particularly advantageous in that it allows the flow rate to be set to a desired flow rate within a broad continuum of flow rates, unlike prior art pumps which use a constant flow rate and which actively control the delivery of fluid by monitoring and controlling the amount of time that the valve remains open, or which have a limited number of preset flow rates. This is due to the use of the restrictor member, which can partially or completely restrict some of all of the lumens of the multi-lumen member. The present invention is therefore further advantageous in that it requires a minimal amount of energy to operate the pump. In particular, since the flow rate mechanism only requires energy while it is being adjusted to a certain rate, it does not require a continuous supply of energy while the pump is operating, unlike most prior art pumps which use an active pumping mechanism or an active valve to control flow rate. The flow rate of the valve of the present invention can be directly adjusted by setting the restrictor member such that the pump is operating at a desired flow rate, energy is not required to continuously monitor and control the amount of time that the valve remains open. The present invention is also particularly advantageous in that it allows the use of additional power-consuming features, such as sensors, since the valve requires little energy to operate.

Figure 1A:
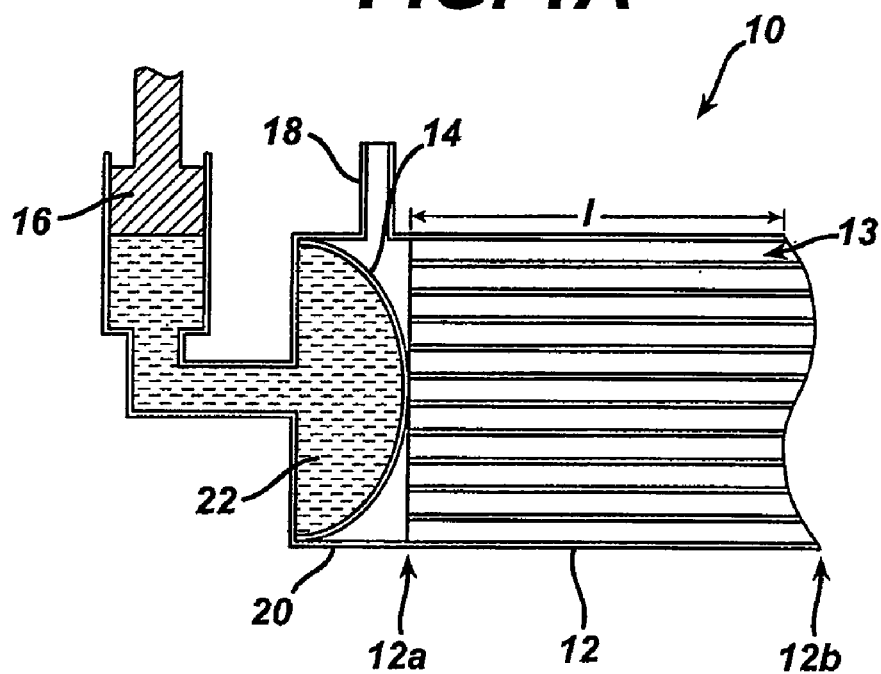
FIG. 1A is an illustration of one embodiment of a valve for controlling the flow rate of fluid from an implantable pump.

FIG. 1A illustrates one embodiment of a valve 10 for controlling fluid flow from an implantable drug delivery pump. As shown, the valve 10 generally includes a multi-lumen member 12 and a restrictor member 14 that is adapted to selectively restrict at least a portion of one or more lumens extending through the multi-lumen member 12 to thereby adjust the flow of fluid therethrough. The valve 10 further includes an actuator mechanism 16 that can be used to control the restrictor member 14.

Figure 1B:
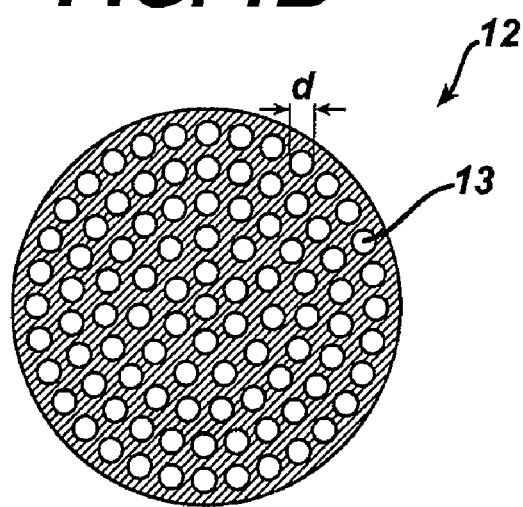
FIG. 1B is a cross-sectional view of the multi-lumen capillary tube of the valve show in FIG. 1A.

The multi-lumen member 12 can have a variety of configurations, but in an exemplary embodiment the multi-lumen member 12 is a capillary tube having several lumens extending between opposed first and second ends 12a, 12b, a cross-section of which is shown in FIG. 1B. The first end 12a is coupled to a valve inlet 18 that is adapted to receive fluid flow from an implantable pump, and the second end 12b forms an outlet for delivering fluid to a patient, e.g., via a catheter coupled to or otherwise associates with the second end 12b. The capillary tube 12 can be formed from a variety of materials, and it can have a variety of shapes and sizes. The capillary tube 12 should, however, have a shape and size that enables it to deliver very small amounts of fluid, preferably in the range of about 0 mL to 4 mL per day, and that enables it to be either implanted within a drug delivery pump or within a catheter connected to a drug delivery pump. In an exemplary embodiment, the capillary tube 12 is formed from ductile glass material that is assembled to have an essentially round outer cross section and multiple lumens 13, preferably with diameters d of about 250 micrometers or less. The number of lumens 13, as well as the length l of the tube 12, can vary depending on the desired flow parameters. One example of a suitable capillary tube for use with the present invention is available from Nine Sigma, Inc. of Cleveland, Ohio.

As previously stated, the valve 10 also includes a restrictor member 14 which can have a variety of configurations, but which should be adapted to selectively restrict at least a portion of one or more lumens 13 in the capillary tube 12. The restrictor member 14 can be disposed adjacent to the second end 12b of the multi-lumen capillary tube 12, or alternatively it can be disposed adjacent to the first end 12a of the capillary tube 12 as shown in FIG. 1A. While the configuration of the restrictor member 14 can vary, in an exemplary embodiment the restrictor member 14 is formed from a flexible membrane 14 that extends across a housing 20 that is coupled to the first end 12a of the capillary tube 12. The housing 20 is effective to create a sealed connection with the first end 12a of the capillary tube 12, and it includes a valve inlet port 18 formed therein for allowing fluid to be delivered to the capillary tube 12 from a pump reservoir. The membrane 14 is disposed across a portion of the housing 20 such that the membrane 14 does not block the inlet port 18, yet the membrane 14 can be expanded, inflated, or otherwise moved to restrict at least a portion of one or more lumens 13 in the capillary tube 12. The materials used to form the membrane will vary depending on the configuration of the actuator mechanism. In an exemplary embodiment, however, the membrane 14 is formed from an elastomeric silicone rubber, polyurethane, or any other flexible material.

Figure 2:
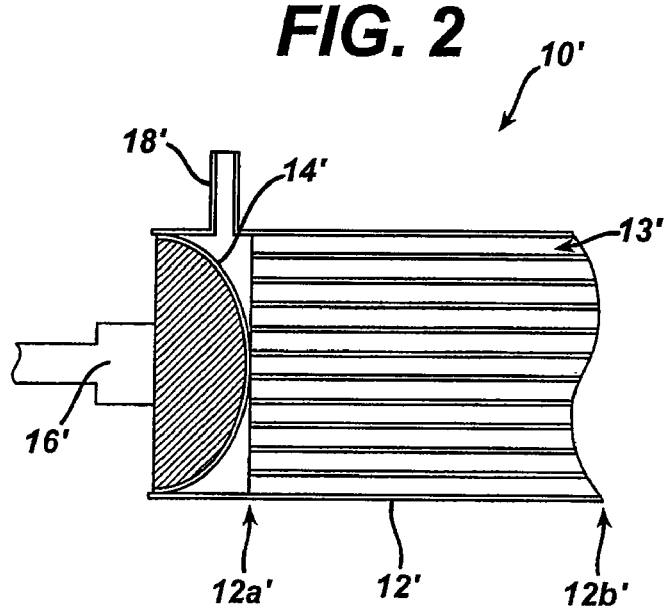
FIG. 2 is an illustration of another embodiment of a valve for controlling the flow rate of fluid from an implantable pump.

A variety of techniques can be used to actuate the membrane 14 to restrict at least a portion of one or more lumens in the capillary tube 12. In the embodiment illustrated in FIG. 1A, the membrane 14 forms a balloon-like structure or sealed cavity 22 in the housing 20 to allow the membrane 14 to be inflated and deflated by the actuator mechanism 16. The actuator mechanism 16 in this embodiment is preferably a hydraulic actuator 16 that can move to cause fluid or air disposed within the cavity 22 to inflate or deflate the membrane 14. Accordingly, the membrane 14 is preferably sufficiently flexible to allow the membrane 14 to be easily inflated and deflated. In an alternative embodiment, shown in FIG. 2, a mechanical actuator mechanism 16' can be used to directly control movement of the membrane 14'. In particular, a piston-type member 16' can be used to apply a direct force to the membrane 14' to cause the membrane 14' to restrict at least a portion of one or more lumens 13' in the capillary tube 12'. In this embodiment, the membrane 14' is preferably thicker and less flexible than the inflatable membrane 14 illustrated in FIG. 1A.

A person skilled in the art will appreciate that a variety of other techniques can be used to cause the membrane 14 to restrict at least a portion of one or more lumens 13 in the capillary tube 12. Moreover, the restrictor member 14 is not limited to a flexible membrane 14, but rather it can have any configuration that allows one or more lumens 13 in the capillary tube 12 to be selectively restricted.

Movement of the actuator mechanism 16 can be accomplished using a variety of techniques. Exemplary techniques for moving the actuator mechanism 16 include, for example, a motor with gears and piezoelectric materials. The actuator mechanism 16 should, however, be remotely controllable, e.g., using telemetry, to allow the flow rate to be adjusted after the valve is implanted. A variety of techniques are known in the art for providing a telemetry-controlled actuator mechanism 16.

In use, the valve 10 is coupled to an implantable drug delivery pump such that it is disposed between the fluid reservoir in the pump and the outlet in the catheter where fluid is delivered to the patient. The flow rate can be adjusted by simply moving the actuator mechanism to cause membrane 14 to either cover a number of lumens 13 in the capillary tube 12 to decrease the flow rate of fluid through the capillary tube 12, or alternatively to uncover a number of lumens 13 in the capillary tube 12 to increase the flow rate of fluid through the capillary tube 12.

Figure 3:
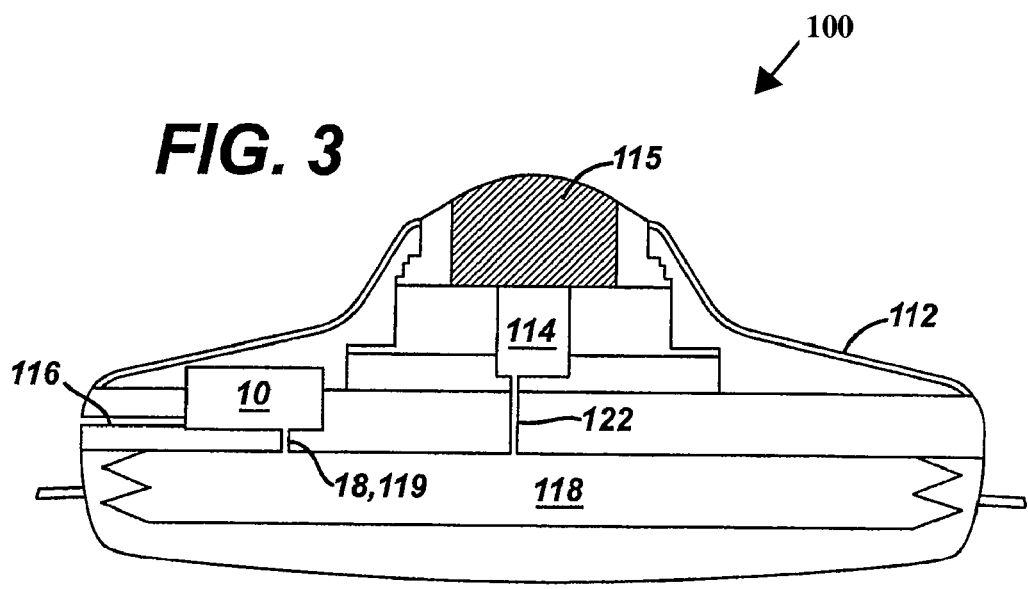
FIG. 3 is a cross-sectional view of one embodiment of an implantable drug delivery pump according to the present invention.

As previously stated, the valve 10 can either be implanted within a drug delivery pump, or alternatively it can be disposed within a catheter that is connected to a drug delivery pump. When implanted in a catheter, the valve 10 should be configured such that all fluid that flows through the catheter is required to pass through the valve, thus allowing the fluid flow rate to be controlled. In an exemplary embodiment, however, the valve is disposed within an implantable drug delivery pump 10, as shown in FIG. 3. A person skilled in the art will appreciate that the pump 10 is merely intended as an exemplary embodiment of an implantable drug delivery pump, and that the present invention techniques for controlling the flow rate can be incorporated into any implantable pump or other fluid delivery device.

As shown, the implantable drug pump 100 generally includes a housing 112 having a pump inlet port 114 and a pump outlet port 116, each of which are fluidly coupled to a reservoir 118 formed within the housing 112 for retaining a fluid, e.g., a drug, therein. Fluid can be introduced into the reservoir 118 through the pump inlet port 114 via a reservoir inlet port 122. As shown, a septum 115 is formed on the top of the pump 100 to allow refilling of the reservoir 118 through the pump inlet port 114. Fluid can exit the reservoir 118 through the pump outlet port 116 via the reservoir outlet port 119. The reservoir 118 in the pump 100 is preferably formed from a bellows that is compressible upon application of a force thereto by a driver mechanism that is effective to selectively drive fluid from the reservoir 118 to the pump outlet port 116. A variety of driver mechanisms can be used, but in one embodiment the driver mechanism is a constant-pressure driver mechanism.

The valve 10 is disposed between the reservoir 118 and the pump outlet port 116, and more particularly, the valve inlet port 18 is connected to the reservoir outlet port 119 and the second end 12b of the capillary tube 12 is connected to the pump outlet port 116. In use, the driver mechanism can apply a constant pressure to the reservoir 118 to force fluid to exit the reservoir 118 via the reservoir outlet port 119, whereby the fluid flow rate is controlled by the valve 10, as previously discussed. The flow rate can be adjusted by actuating the restrictor member 14 to cover/uncover additional lumens 13 in the capillary tube, as previously described.

Figure 4:
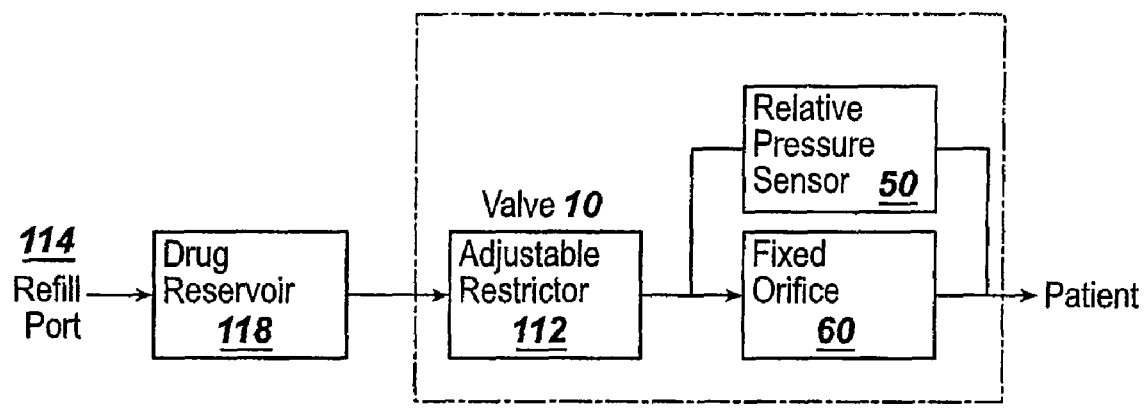
FIG. 4 is a diagram showing a pressure sensor used in connection with an adjustable valve in accordance with yet another embodiment of the present invention.

In yet another embodiment of the present invention, a sensor can be used to provide closed-loop feedback for control of the pump flow rate, and/or to sense/measure a variety of other conditions. Virtually any sensor can be provided, and it can be placed within the pump or within the fluid-delivery catheter that is coupled to the pump outlet port 116. In an exemplary embodiment, the sensor is preferably a pressure sensor that is adapted to measure the pressure of fluid flowing from the valve 10 to the patient. FIG. 4 is a diagram illustrating an exemplary configuration of the implantable drug pump 100 of FIG. 3 having a differential pressure sensor 50 disposed downstream of the valve 10 for determining the flow rate of fluid flowing from the valve 10 to the patient's body. Virtually any pressure sensor 50 can be used, but the pressure sensor 50 is preferably disposed across a fixed orifice 60 that is pre-calibrated. The fixed orifice 60 can have a variety of configurations, and in one embodiment it can be formed from, for example, a capillary tube that is similar to capillary tube 12 that forms the restrictor member. Alternatively, the fixed office can be made using micro-electro-mechanical systems (MEMS) technology such that the orifice is a chip capillary and the differential pressure sensor is integral with the chip. In use, the sensor can be relied on to adjust the restrictor member 14 to produce the necessary flow rate of fluid being delivered to the patient.

A person skilled in the art will appreciate that the pump can include a variety of other features not shown or described herein. By way of non-limiting example, the pump can include a bolus port in fluid communication with the outlet port. In use, fluid can be injected into the bolus port, whereby it flows directly out of the outlet port and is delivered to the patient. The pump can also optionally include one or more filters that are effective to prevent the accumulation of debris, for example, at the first end 12a of the capillary tube 12.

One skilled in the art will appreciate further features and advantages of the invention based on the above-described embodiments. Accordingly, the invention is not to be limited by what has been particularly shown and de cribed, except as indicated by the appended claims. All publications and references cited herein are expressly incorporated herein by reference in their entirety.

What is claimed is:

1. A valve adapted to control the flow rate of fluid flow from an implantable pump, comprising:
   a multi-lumen member disposed within a housing and adapted to receive fluid-flow therethrough between a first end coupled to an inlet and a second end coupled to an outlet; and
   a restrictor member that prevents fluid that is flowing from the inlet to the outlet from flowing through the restrictor member without blocking the inlet, the restrictor member extending across the housing and sealed around a perimeter of the housing, and the restrictor member being coupled to the multi-lumen member such that the restrictor member is effective to selectively restrict at least a portion of one or more lumens in the multi-lumen member to thereby adjust the flow rate of fluid flowing through the multi-lumen member.

2. The valve of claim 1, wherein the multi-lumen member comprises a multi-lumen capillary tube.

3. The valve of claim 2, wherein the inlet coupled to the first end of the multi-lumen member comprises an inlet port for receiving fluid flow from an implantable pump, and the outlet coupled to the second end of the multi-lumen member comprises an outlet port for delivering fluid to a fluid-delivery catheter.

4. The valve of claim 3, wherein the restrictor member comprises a flexible membrane disposed adjacent to one of the first end or the second end of the capillary tube, the flexible membrane being effective to selectively restrict at least a portion of one or more lumens in the capillary tube.

5. The valve of claim 4, further comprising an actuator mechanism for applying pressure to the flexible membrane to selectively restrict at least a portion of one or more lumens in the capillary tube.

6. The valve of claim 5, wherein the actuator mechanism comprises a mechanical or electromechanical member.

7. The valve of claim 4, wherein the flexible membrane is expandable to selectively restrict at least a portion of one or more lumens in the capillary tube.

8. The valve of claim 4, wherein the flexible membrane is coupled to the housing to form a balloon-like structure such that the flexible membrane is inflatable to selectively restrict at least a portion of one or more lumens in the capillary tube.

9. The valve of claim 8, further comprising a hydraulic pump coupled to the flexible membrane and effective to at least one of inflate or deflate the flexible membrane.

10. The valve of claim 9, further comprising an actuator mechanism coupled to the hydraulic pump for selectively actuating the hydraulic pump, the actuator mechanism being operable by telemetry.

11. The valve of claim 1, wherein the multi-lumen member includes two or more lumens that each extend from the first end to the second end.

12. The valve of claim 1, wherein the first end and the second end of the multi-lumen member are opposed.

13. A method for controlling the flow rate of fluid being delivered to a patient from an implantable pump, comprising:
   providing a valve in fluid communication with a reservoir formed in an implantable pump, the valve including a multi-lumen member disposed within a valve housing and coupled to a restrictor member extending across the valve housing and sealed around a perimeter of the housing, the restrictor member preventing fluid flowing from an inlet to an outlet from flowing through the restrictor member without blocking the inlet, and selectively restricting at least a portion of one or more lumens in the multi-lumen member to thereby adjust the flow rate of fluid flowing from the reservoir between a first end of the multi-lumen member coupled to the inlet and a second end of the multi-lumen member coupled to the outlet; and
   actuating the restrictor member to selectively restrict at least a portion of one or more lumens to thereby adjust the flow rate of fluid flowing from the reservoir.

14. The method of claim 13, wherein the inlet coupled to the first end of the multi-lumen member comprises an inlet port for receiving fluid flow from an implantable pump, and the outlet coupled to the second end of the multi-lumen member comprises an outlet port for delivering fluid to a fluid-delivery catheter.

15. The method of claim 13, wherein the restrictor member comprises a flexible membrane disposed adjacent to one of the first end or the second end of the multi-lumen member, the flexible membrane being effective to selectively restrict at least a portion of one or more lumens in the multi-lumen member.

16. The method of claim 15, further comprising an actuator mechanism for applying pressure to the flexible membrane to selectively restrict at least a portion of one or more lumens in the multi-lumen member.

17. The method of claim 16, wherein the actuator mechanism comprises a mechanical or electromechanical member.

18. The method of claim 15, wherein the flexible membrane is expandable to selectively restrict at least a portion of one or more lumens in the multi-lumen member.

19. The method of claim 15, wherein the flexible membrane is coupled to the valve housing to form a balloon-like structure such that the flexible membrane is inflatable to selectively restrict at least a portion of one or more lumens in the multi-lumen member.

20. The method of claim 19, further comprising a hydraulic pump coupled to the flexible membrane and effective to at least one of inflate or deflate the flexible membrane.

21. The method of claim 20, further comprising an actuator mechanism coupled to the hydraulic pump for selectively actuating the hydraulic pump, wherein the actuator mechanism is operable by telemetry.

* * * * *